United States Patent [19]

Rose et al.

[11] 4,226,595

[45] Oct. 7, 1980

[54] OXIDATION HAIR-COLORING PREPARATION BASED UPON N,N-BIS-($\beta$-HYDROXYETHYL)-m-PHENYLENEDIAMINES

[75] Inventors: David Rose, Hilden; Edgar Lieske, Düsseldorf; Peter Busch, Erkrath, all of Fed. Rep. of Germany

[73] Assignee: Henkel Kommanditesellschat auf Aktien, Düsseldorf-Holthausen, Fed. Rep. of Germany

[21] Appl. No.: 972,012

[22] Filed: Dec. 21, 1978

[30] Foreign Application Priority Data

Dec. 27, 1977 [DE] Fed. Rep. of Germany ....... 2758203

[51] Int. Cl.$^2$ ................................................. A61K 7/13
[52] U.S. Cl. ......................................... 8/406; 8/408; 8/414
[58] Field of Search ............................... 8/10.2, 11, 32

[56] References Cited

U.S. PATENT DOCUMENTS

| | | | |
|---|---|---|---|
| 3,642,423 | 2/1972 | Bil et al. | 8/10.1 |
| 3,920,384 | 11/1975 | Feinland et al. | 8/10.2 |
| 3,970,423 | 7/1976 | Brody et al. | 8/10.2 |
| 3,981,678 | 9/1976 | Ghilardi et al. | 8/10.2 |
| 4,092,102 | 5/1978 | Halasz et al. | 8/10.2 |
| 4,125,367 | 11/1978 | Bugaut et al. | 8/10.2 |
| 4,125,601 | 11/1978 | Bugaut et al. | 8/10.2 |
| 4,129,414 | 12/1978 | Rose et al. | 8/10.2 |

FOREIGN PATENT DOCUMENTS

| | | | |
|---|---|---|---|
| 802554 | 10/1958 | United Kingdom | 8/10.2 |
| 805746 | 12/1958 | United Kingdom | 8/10.2 |
| 1186267 | 4/1970 | United Kingdom | . |

*Primary Examiner*—Allen J. Robinson
*Attorney, Agent, or Firm*—Hammond & Littell, Weissenberger and Muserlian

[57] ABSTRACT

An aqueous hair dye preparation comprising an oxidation dyestuff combination of a developer component and a coupler component consisting of an N,N-bis-($\beta$-hydroxyethyl)-m-phenylenediamine as well as a process for dyeing hair by utilizing this oxidation dyestuff combination.

16 Claims, No Drawings

OXIDATION HAIR-COLORING PREPARATION BASED UPON N,N-BIS-(β-HYDROXYETHYL)-m-PHENYLENEDIAMINES

THE PRIOR ART

Of great importance for the dyeing of hair are the so-called oxidation dyestuffs because of their intense colors and very good fastness. These dyestuffs are formed by the oxidative coupling of a developer component with a coupling component. The developers customarily used are nitrogenous bases, such as p-phenylenediamine derivatives, diaminopyridines, 4-aminopyrazolone derivatives or heterocyclic hydrazones. Useful as so-called coupling components are phenols, naphthols, resorcinol derivative and pyrazolones.

Good oxidation dyestuff components for hair dyeing must fulfill all of the following requirements.

They have to be able to develop a sufficient intensity of the desired color shades when oxidatively coupled with the respective developer component or coupling component. Furthermore, they have to possess a capacity for being absorbed by human hair, which capacity ranges from sufficient to very good; and in addition, they should be unobjectionable from toxicological and dermatological view points.

Furthermore, it is important that strong shades closely corresponding to the natural color nuances of the hair be obtained on the hair to be dyed. In addition, the general stability and safety of the formed dyes as well as their fastness to light and shampooing and their thermostability are particularly important to prevent color shifts away from the original chosen and desired nuance or even changes to other shades.

Thus it is particularly important to provide suitable oxidation hair coloring components and compositions which meet all the requirements for oxidation hair-dyes with respect to safety, toxicological and dermatological, as well as providing fastness stability and permanence.

OBJECTS OF THE INVENTION

An object of the invention is to provide usable oxidation hair dyes containing suitable components which optimally satisfy the above requirements.

Another object of the present invention is to provide an oxidation dyestuff combination of a developer component and a coupling component which is based on certain N,N-bis-(β-hydroxyethyl)-m-phenylenediamines as the coupler component.

These and further objects of the present invention will become apparent as the description thereof proceeds.

DESCRIPTION OF THE INVENTION

The present invention provides a composition and process for dyeing hair based upon an oxidation dyestuff combination of developers and a coupling component which is an N,N-bis-(β-hydroxyethyl)-m-phenylenediamine. It has now been found that the above-specified requirements can be fulfilled to an especially significant extent by the use of hair coloring preparations that are based on oxidation dyestuff combinations containing N,N-bis-(β-hydroxyethyl)-m-phenylenediamines of the formula (I)

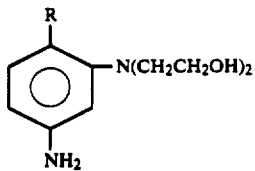

where R represents hydrogen or an alkoxy group, the alkyl portion of which contains 1–4 C atoms, as well as their inorganic or organic salts, as coupling agents and the developer components usually present in oxidation hair colorings.

Used as coupling components, the compounds according to the invention yield very intense hues reaching from yellowish brown to violet together with the developers generally employed for oxidation hair coloring and they thus represent an important addition to the possibilities in the oxidative coloring of hair. Beyond this, the N,N-bis-(β-hydroxyethyl)-m-phenylenediamines according to the invention are characterized by a very good fastness of the colors achieved with them, a good water-solubility, a good shelf life and toxicological as well as dermatological safety.

The N,N-bis-(β-hydroxyethyl)-m-phenylenediamines can be used as they are or used in the form of their salts with inorganic or organic acids, e.g. as chlorides, sulfates, phosphates, acetates, propionates, lactates, citrates.

The N,N-bis-(β-hydroxyethyl)-m-phenylenediamines to be used as coupling components according to the invention represent compounds known from the literature that can be prepared by the cleavage of acid from the corresponding commercial N-acetyl compounds for example:

N,N-bis-(β-hydroxyethyl)-m-phenylenediamine and 2-methoxy-5-amino-N,N-bis-(β-hydroxyethyl)-aniline, 2-ethoxy-5-amino-N,N-bis-(β-hydroxyethyl)-aniline, 2-propoxy-5-amino-N,N-bis-(β-hydroxyethyl)-aniline and 2-butoxy-5-amino-N,N-bis-(β-hydroxyethyl)-aniline can be mentioned as coupling components to be used according to the invention.

As examples for the developer components to be used in the hair coloring preparations according to the invention there may be mentioned primary aromatic amines with one additional functional group in the p-position such as: p-phenylenediamine, p-toluenediamine, p-aminophenol, N-methyl-p-phenylendiamine, N,N-dimethyl-p-phenylenediamine, N,N-diethyl-2-methyl-p-phenylenediamine, N-ethyl-N-hydroxyethyl-p-phenylenediamine, chloro-p-phenylenediamine, N,N-bis-hydroxyethylamino-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine; other compounds of the mentioned type further containing one or several functional groups such as OH groups, $NH_2$ groups, NHR groups, where R represents an alkyl or hydroxyalkyl radical with 1–4 C atoms; diaminopyridine derivatives; heterocyclic hydrazone derivatives such as 1-methyl-pyrrolidone-(2)-hydrazone; 4-aminopyrazolone derivatives such as 4-amino-1-phenyl-3-carbamoylpyrazolone-5;N-butyl-N-sulfobutyl-p-phenylenediamine; tetraaminopyrimidines such as 2,4,5,6-tetraaminopyrimidine, 4,5-diamino2,6-bis-methylamino-pyrimidine, 2,5-diamino-4-diethylamino-6-methylaminopyrimidine, 2,4,5-triamino-6- dimethylaminopyrimidine, 2,4,5-triamino-6-piperidinopyrimidine, 2,4,5-triamino-6-anilinopyrimidine, 2,4,5-triamino-6-morpholinopyrimidine, 2,4,5-triamino-6-β-hydroxyethylaminopyrimidine; etc.

A blue dye of high value is especially important as a nuance or shading component to obtain strong color shades that correspond as much as possible to the natural blending of hair colors. Difficulties are frequently encountered in the creation of natural color nuances when using the conventional blue coupling agents. The use of the N,N-bis-(β-hydroxyethyl)-m-phenylenediamines as coupling agents according to the invention largely overcomes such difficulties. These coupling components produce, together with the respective developers, especially intense dark blue to black-blue hair colors in addition to other nuances that are all characterized by extreme light fastness.

In the hair coloring preparations according to the invention the coupling components are generally used in substantially molar amounts, with respect to the developers. Although equimolar amounts are preferred, it is possible to use more or less of either component in the molar range 2:1 to 1:2, more preferably up to 10% excess or deficiency.

Furthermore, it is not necessary that each of the developing component and the coupling substances be a single substance since the developing components may be mixtures of the developer compounds to be used according to the invention and the coupling substances may be mixtures of N,N-bis-(β-hydroxyethyl)-m-phenylenediamines according to the invention.

The hair coloring combinations according to the invention may also contain, if desired, admixed customary conventional hair dyes, i.e., hair coloring compositions or dyestuffs, that are also hair substance, if necessary for the creation of certain shades and nuances. Up to 5% of direct dyes may be used together with conventional oxidative dyes.

Some examples of other customary developers are p-phenylenediamine derivatives, diaminopyridines, 4-amino-pyrazolone derivatives and heterocyclic hydrazones. Some examples of other customary couplers are phenols, naphthols, resorcinol derivatives and pyrazolones. In addition to the above listed components, other conventional developers and couplers will be readily apparent to those skilled in the art.

The oxidative coupling, i.e., the development of the color, is principally possible with atmospheric oxygen, as is the case with other oxidation hair dyes. However, the use of chemical oxidizing agents is often advantageous. Hydrogen peroxide or its addition products with urea, melamine and sodium borate as well as mixtures of such hydrogen peroxide addition compounds and potassium peroxide disulfate are especially useful when chemical oxidizing agents are desired.

The hair dyes according to the invention may be applied by adding them to suitable cosmetic vehicles such as creams, emulsions, jellies or simple solutions and may be mixed with one of the mentioned oxidizing agents immediately before their application to the hair. The concentration of the coupler-developer combination in the vehicle of such preparations is 0.2% to 5% by weight, preferably 1% to 3% by weight.

For the preparation of creams, emulsions or jellies, the dye components are mixed with the other ingredients usually used for such products. To be mentioned as such additional ingredients are, for example, wetting or emulsifying agents of the anionic or nonionic type such as alkylbenzene-sulfonates, sulfates of higher fatty alcohols, higher alkylsulfonates, higher fatty acid alkanolamides, addition products of ethylene oxide on higher fatty alcohols; thickeners such as methyl cellulose, starch, higher fatty alcohols, paraffin oil, and higher fatty acids. Further perfume oils and hair care products such as pantothenic acid and cholesterol may be included.

The above-mentioned adjuvants and additives are used in the amounts customarily used for such purposes. For example effective amounts of wetting and emulsifying agents range from 0.5% to 30% by weight of thickeners are used in concentrations of 0.1% to 25% by weight, based in each case on the total weight of the entire preparation.

The hair coloring preparations according to the invention may be applied in a weakly acid, neutral or preferably in an alkaline medium at a pH of 8 to 10, regardless of whether it is applied from a vehicle in the form of a solution, emulsion, cream or jelly.

The hair coloring preparations are applied at a temperature which usually ranges from 15° to 40° C. but preferably at room temperature.

After the preparation has been allowed to react for about 30 minutes, the hair coloring preparation is removed from the hair by rinsing. The hair is then washed with a mild shampoo and dried.

The following examples are merely illustratve of the product according to the present invention without being deemed limitative of its scope in any manner.

EXAMPLES

The compounds mentioned below were used as the couplers in the following examples but any of the other compounds according to the formula (I) may be used with equivalent results:

A: N,N-bis-(β-hydroxyethyl)-m-phenylenediamine;
B: 2-methoxy-5-amino-N,N-bis-(β-hydroxyethyl)-aniline;
C: 2-ethoxy-5-amino-N,N-bis-(β-hydroxyethyl)-aniline.

The following substances were used as developing components in the Examples hereinafter:

E1: p-phenylenediamine
E2: p-toluylenediamine
E3: p-aminophenol
E4: N,N-dimethyl-p-phenylenediamine
E5: 2-piperidino-4,5,6-triaminopyrimidine
E6: 1-methylpyrrolidon-(2)-hydrazone
E7: 1-phenyl-3-carbamoyl-4-aminopyrazolone
E8: N,N-bis-(β-hydroxyethylamino)-p-phenylenediamine
E9: N-butyl-N-sulfobutyl-phenylenediamine
E10: 2,4,5,6-tetraaminopyrimidine
E11: 2-chloro-1,4-diaminobenzene The hair dyes according to the invention were used in the form of a cream emulsion.

Into an emulsion of
10 parts by weight of fatty alcohols with the chain length $C_{12}$–$C_{18}$
10 parts by weight of the sulfate (sodium salt) of fatty alcohol with the chain length $C_{12}$–$C_{18}$
75 parts by weight water were incorporated 0.01 mol of one of the developers listed in the table below and 0.01 mol of the N,N-bis-(β-hydroxyethyl)-m-phenylenediamine. Then, the pH of the emulsion was adjusted to 9.5 with ammonia, and the emulsion was made up to 100 parts by weight with water. The oxidative coupling was performed either with atmospheric oxygen or with a 1% hydrogen peroxide solution as the oxidizing agent, adding 10 parts by weight of the hydrogen peroxide solution to 100 parts by weight of emulsion. The respective composition cream were applied with or without an additional oxidizing agent to human hair. The hair was 90% gray and not specially pretreated. The application were allowed to remain on the hair for 30 minutes to complete the coloring. Upon completion of the hair coloring process, the hair was washed with a conventional shampoo and then dried. The shades obtained in this manner are recorded in Table 1.

TABLE 1

| Example # | Developer | Coupler | Resulting Shade By air oxidation | By oxidation with 1% solution of $H_2O_2$ |
|---|---|---|---|---|
| 1 | E1 | A | Dark Blue | Dark Blue |
| 2 | E2 | A | Dark Blue | Dark Blue |
| 3 | E3 | A | Gray Ruby | Gray Magenta |
| 4 | E4 | A | Dark Blue | Dark Blue |
| 5 | E5 | A | Brown | Red Brown |
| 6 | E6 | A | Yellow Brown | Brown Orange |
| 7 | E7 | A | Dark Blue | Dark Blue |
| 8 | E8 | A | Dark Blue | Dark Blue |
| 9 | E9 | A | Gray Tourquoise | Dark Blue |
| 10 | E10 | A | Olive Brown | Olive Brown |
| 11 | E1 | B | Black Blue | Black Blue |
| 12 | E3 | B | Violet Brown | Red Brown |
| 13 | E4 | B | Dark Blue | Dark Blue |
| 14 | E5 | B | Flat Green | Flat Green |
| 15 | E6 | B | Yellow Brown | Brown Orange |
| 16 | E7 | B | Blue Gray | Blue Gray |
| 17 | E10 | B | Dark Green | Green |
| 18 | E8 | B | Dark Blue | Dark Blue |
| 19 | E9 | B | Flat Blue | Flat Blue |
| 20 | E11 | B | Gray Violet | Flat Violet |
| 21 | E1 | C | Dark Blue | Dark Blue |
| 22 | E2 | C | Dark Blue | Dark Blue |

The preceding specific embodiments are illustrative of the practice of the invention. It is to be understood however, that other expedients known to those skilled in the art or disclosed herein, may be employed without departing from the spirit of the invention or the scope of the appended claims.

We claim:

1. An oxidation hair coloring composition consisting essentially of, as coupling agent at least one compound selected from the group of N,N-bis-(β-hydroxyethyl)-m-phenylenediamines having the formula I

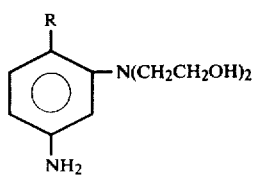

wherein R represents hydrogen or an alkoxy group, the alkyl portion of which contains one to four carbon atoms, and the water-soluble hair compatible organic or inorganic salts thereof; and a water-soluble developer therefor, said developer and said coupling agent being present in the molar range of 2:1 to 1:2.

2. An aqueous emulsion for the dyeing of hair having a content of 0.2% to 5% by weight of the coupling agent-developer composition of claim 1.

3. The emulsion according to claim 2 having a pH in the range of 8 to 10.

4. The composition according to claim 1 wherein said developer is at least one nitrogen-based conventional developer component usually present in oxidation hair colorings.

5. An aqueous preparation of the developer-oxidizer type for the dyeing of hair, comprising 0.2% to 5% by weight of the coupling agent-developer combination of claim 1; from 0% to 30% by weight of a surfactant; from 0% to 25% by weight of a thickener; and the remainder water.

6. The aqueous preparation of claim 5 wherein said coupling agent-developer combination is present in an amount of from 1% to 3% by weight.

7. The composition according to claim 1 wherein said proportion of coupling agent to developer is substantially 1:1.

8. The composition according to claim 1 wherein said coupling agent component is selected from the group consisting of N,N-bis-(β-hydroxyethyl)-m-phenylenediamine, 2-methoxy-5-amino-N,N-bis-(β-hydroxyethyl)-aniline, 2-ethoxy-5-amino-N,N-bis-(β-hydroxyethyl)-aniline, 2-propoxy-5-amino-N,N-bis-(β-hydroxyethyl)-aniline, and 2-butoxy-5-amino-N,N-bis-(β-hydroxyethyl)-aniline.

9. The composition according to claim 8 wherein said coupling agent component is selected from the group consisting of N,N-bis-(β-hydroxyethyl)-m-phenylenediamine, 2-methoxy-5-amino-N,N-bis-(β-hydroxyethyl)-aniline, and 2-ethoxy-5-amino-N,N-bis-(β-hydroxyethyl)-aniline.

10. The composition according to claim 1 wherein said developer agent is at least one developer compound selected from the group consisting of:
p-phenylenediamine
p-toluylenediamine
p-aminophenol
N,N-dimethyl-p-phenylenediamine
piperidino-4,5,6-triaminopyrimidine
1-methylpyrrolidon-(2)-hydrazone
1-phenyl-3-carbamoyl-4-aminopyrazolone
N,N-bis-(β-hydroxyethylamino)-p-phenylenediamine
N-butyl-N-sulfobutyl-p-phenylenediamine
2,4,5,6-tetraaminopyrimidine, and
2-chloro-1,4-diaminobenzene 11. The aqueous preparation according to claim 5 wherein said preparation is adjusted to an alkaline range of pH 8 to 10.

12. The process for the coloring of human hair which comprises the step of applying to hair at temperatures in the range 15° C. to 40° C. for a time sufficient to effect dyeing through oxidation, an effective amount of the aqueous preparation according to claim 5.

13. The process according to claim 12 wherein an oxidizer component is added to said aqueous preparation just prior to the application to the hair, and the hair is rinsed after effecting the dyeing.

14. An oxidation hair coloring composition consisting essentially of, as coupling agent at least one compound selected from the group of N,N-bis-(β-hydroxyethyl)-m-phenylenediamines having the formula I

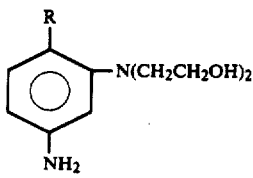

wherein R represents hydrogen or an alkoxy group, the alkyl portion of which contains one to four carbon atoms, and the water-soluble hair compatible organic or inorganic salts thereof; and a water-soluble, nitrogen-based developer therefor selected from the group consisting of a p-phenylenediamine derivatives, diaminopyridines, 4-aminopyrazolone derivatives, heterocyclic hydrazone derivatives, and tetraaminopyrimidines, said developer and said coupling agent being present in the molar range of 2:1 to 1:2.

15. An aqueous preparation of the developer-oxidizer type for the dyeing of hair, comprising 0.2% to 5% by weight of the coupling agent-developer combination of claim 14; from 0% to 30% by weight of a surfactant; from 0% to 25% by weight of a thickener; and the remainder water.

16. The process for the coloring of human hair which comprises the step of applying to hair at temperatures in the range 15° C. to 40° C. for a time sufficient to effect dyeing through oxidation, an effective amount of the aqueous preparation according to claim 15.

* * * * *